United States Patent [19]

Mailer et al.

[11] 4,196,975
[45] Apr. 8, 1980

[54] AZINE LIQUID CRYSTAL COMPOUNDS FOR USE IN LIGHT-CONTROL DEVICES

[75] Inventors: Hugh Mailer, Lyndhurst; Stanley Laskos, Jr., Diamond, both of Ohio

[73] Assignee: General Electric Company, Syracuse, N.Y.

[21] Appl. No.: 26,781

[22] Filed: Apr. 3, 1979

Related U.S. Application Data

[63] Continuation-in-part of Ser. No. 937,507, Aug. 28, 1978, abandoned, which is a continuation-in-part of Ser. No. 861,954, Dec. 19, 1977, abandoned.

[51] Int. Cl.² .......................... C02F 1/13; C09K 3/34; C07C 119/10; C07C 121/64
[52] U.S. Cl. ............................. 350/350; 252/299; 252/408; 260/465 R; 260/465 E; 260/465 K; 260/566 B; 350/346; 350/349
[58] Field of Search ............. 252/299, 408; 350/346, 350/349, 350; 260/566 B, 465 R, 465 E, 465 K

[56] References Cited

U.S. PATENT DOCUMENTS

| | | | |
|---|---|---|---|
| 2,440,070 | 4/1948 | Blout et al. | 260/566 B |
| 3,947,375 | 3/1976 | Gray et al. | 252/299 |
| 4,001,137 | 1/1977 | Steinstrasser | 252/299 |
| 4,038,200 | 7/1977 | Jones et al. | 252/299 |

OTHER PUBLICATIONS

Kast, Landolt–Bornstein, 6th Edition, vol. 2, Part 2, Springer–Verlag, Berlin, pp. 266–267, 308 (1960).
Usol'Tseva, V.A., et al. Russ. Chem. Rev., vol. 32, No. 9, pp. 495–507 (1963).
Foote, H. W., "Liquid Crystals", International Critical Tables", pp. 314–320 (1926).
Gray, G. W., et al. "Liquid Crystals & Plastic Crystals", vol. 1, John Wiley & Sons, Inc., (1974).

*Primary Examiner*—Teddy S. Gron
*Attorney, Agent, or Firm*—Robert J. Mooney

[57] ABSTRACT

A light-control device includes a liquid crystal material sandwiched between a pair of planar, light-transmitting members. The liquid crystal material particularly includes an asymmetrical azine compound having the general formula:

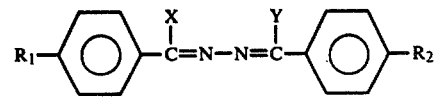

wherein $R_1$ and $R_2$ are different para-substituents selected from the group comprising cyano, halogen, alkyl, and substituted alkyl radicals in which the alkyl radical has from one to nine carbon atoms, and wherein X and Y are selected from the group comprising hydrogen and methyl radicals.

5 Claims, 1 Drawing Figure

AZINE LIQUID CRYSTAL COMPOUNDS FOR USE IN LIGHT-CONTROL DEVICES

This is a continuation-in-part of our application Ser. No. 937,507 filed Aug. 28, 1978, now abandoned and entitled "Azine Liquid Crystal Compounds For Use In Light-Control Devices" which in turn was a continuation-in-part of our application Ser. No. 861,954 filed Dec. 19, 1977, now abandoned.

BACKGROUND OF THE INVENTION

This invention relates generally to the art of visual displays and similar light-control devices and relates more particularly to liquid crystal displays which incorporate an azine compound as part of the system for selective transmission of visible light.

Organic substances which exhibit a mesophase have been known for many years, but it has been only more recently that the technology of liquid crystal materials has been developed sufficiently to achieve commercial application in such devices as wrist watches and digital readouts.

The substances which exhibit a liquid crystal phase, as postulated by Gray and Harrison in U.S. Pat. No. 3,947,374 for example, comprise a molecule with a central linkage group and a pair of distal chemical groups of varying character. These patentees recognize the prior utility of Schiff Bases and themselves disclose commercially useful liquid crystal properties for certain byphenyl compounds. Gray and Harrison also teach that the presence of an unsaturated group in the linkage unit is associated with undesirable, chemical and/or photochemical instability. In addition, Kmetz and Willisen in "Nonemissive Electrooptic Displays," Plenum Press, New York and London (1976), have suggested possible display performance for azine compounds with identical distal groups, although the authors admit that almost nothing is known about the properties of liquid crystal azine compounds.

SUMMARY OF THE INVENTION

Contrary to the teachings and suggestions of the prior art, applicants have discovered that certain azine compounds, despite the presence of two double bonds in the central linkage group, are adequately stable and have other useful properties for display devices. In particular, the azine compounds of the present invention have dissimilar distal groups, i.e. the azine molecule is asymmetric.

Accordingly, a general object of the present invention has been to provide a new class of liquid crystal compounds which have unexpected utility in a variety of light-control devices.

Another object of the present invention is to provide a new class of liquid crystal compounds which are stable and which are easily and economically synthesized.

Applicants have established that a liquid crystal compound which is useful for visual display purposes possesses a melting point of no higher than about 75° C., has a comparatively low viscosity in order to exhibit a short turn-off time, is chemically stable and non-toxic, and shows a high transition temperature from the mesomorphic phase to the isotropic liquid state of at least about 50° C. In order to formulate a material that is acceptable for a given display application, it is sometimes necessary to mix a particular asymmetrical azine compound of the present invention with another like compound or with some other substance, especially to obtain a desired melting point, it having been found that mixtures of some liquid crystal materials have melting points which are depressed to a considerably greater extent than is predictable from simple thermodynamics. On the other hand, the temperatures of transition to isotropic liquid ordinarily vary linearly with molar average composition, between the respective temperatures for the pure components of the mixture.

DESCRIPTION OF THE PREFERRED EMBODIMENTS

Figure 1:
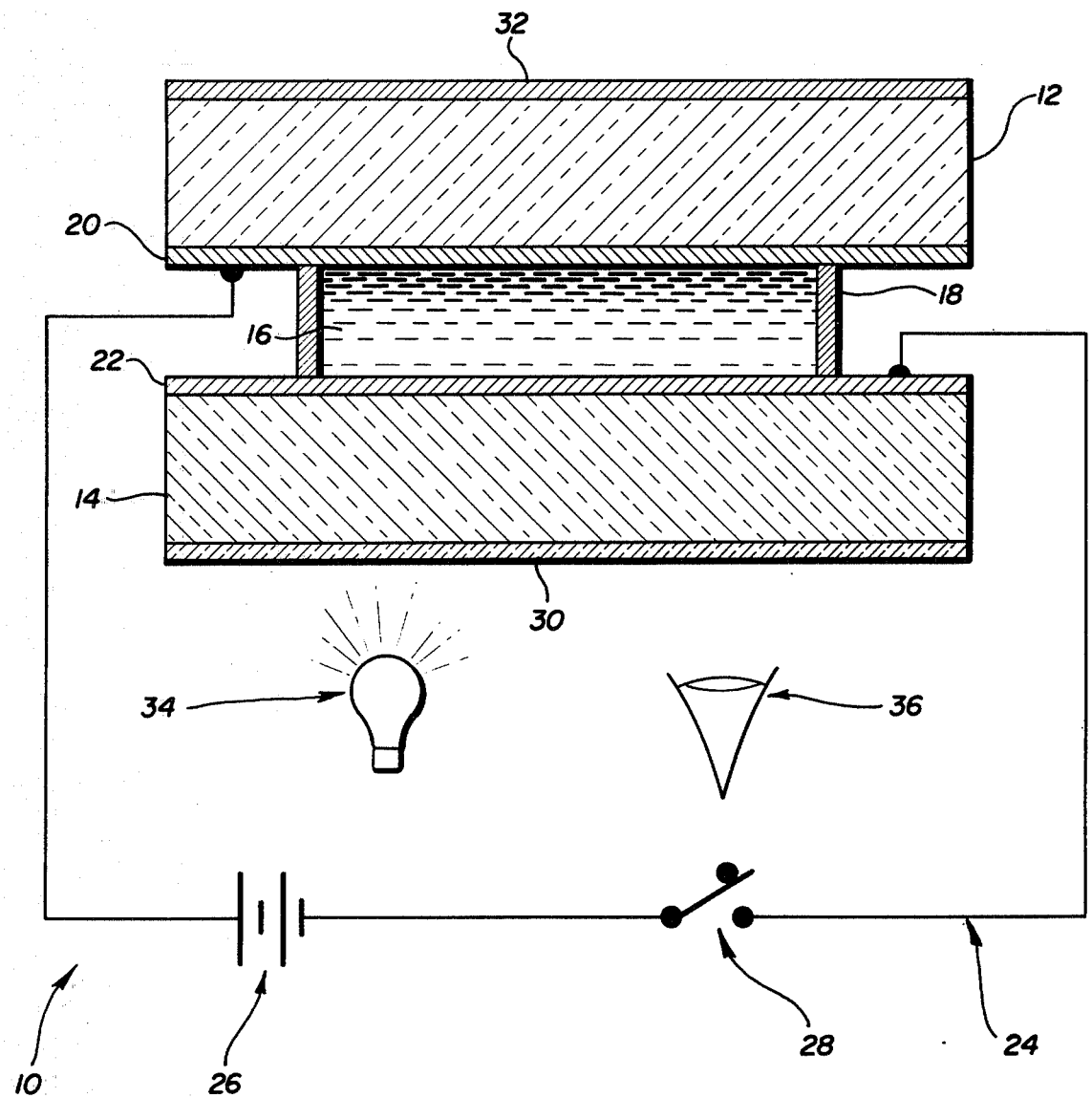

The particular azine compounds of the present invention have the general formula:

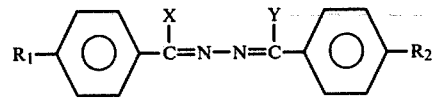

wherein $R_1$ and $R_2$ are different para-substituents whereby to produce an asymmetrical molecular structure, wherein $R_1$ and $R_2$ are selected from the group comprising cyano, halogen, alkyl, and substituted alkyl radicals in which the alkyl radical has from one to nine carbon atoms, and wherein X and Y are selected from the group comprising hydrogen and methyl radicals. The transition temperatures for specific compounds answering this definition and comprising examples of asymmetrical azines which we have specifically synthesized, are set forth in Table I below.

TABLE I
Transition Temperatures For Selected, Asymmetrical Azine Compounds

| $R_1$ | $R_2$ | X | Y | Crystal (or Smectic) to Nematic Transition | Nematic to Isotropic Liquid Transition |
|---|---|---|---|---|---|
| F | n-$C_3H_7$ | $CH_3$ | H | (Sm) 69° C. | 75° C. |
| CN | n-$C_4H_9$ | $CH_3$ | H | (Sm) 56 | 117 |
| CN | n-$C_5H_{11}$ | H | $CH_3$ | 71 | 131 |
| $CH_3$ | n-$C_4H_9$ | H | H | 58 | 87 |
| $CH_3$ | n-$C_5H_{11}$ | H | H | 60 | 100 |
| $CH_3$ | n-$C_7H_{15}$ | H | H | (Sm) 56 | 89 |
| $CH_3$ | n-$C_8H_{17}$ | H | H | 62 | 85 |
| $CH_3$ | n-$C_9H_{19}$ | H | H | 64 | 88 |
| $C_2H_5$ | n-$C_4H_9$ | H | H | 39 | 82 |
| $C_2H_5$ | n-$C_5H_{11}$ | H | H | 32 | 92 |
| $C_2H_5$ | n-$C_6H_{13}$ | H | H | 37 | 82 |
| $C_2H_5$ | n-$C_6H_{13}$ | $CH_3$ | H | 32 | 62 |
| $C_2H_5$ | n-$C_8H_{17}$ | H | H | 33 | 75 |
| n-$C_3H_7$ | n-$C_4H_9$ | H | H | 37 | 95 |
| n-$C_3H_7$ | n-$C_4H_9$ | $CH_3$ | H | 39 | 76 |
| n-$C_3H_7$ | n-$C_4H_9$ | H | $CH_3$ | 44 | 77 |
| n-$C_3H_7$ | n-$C_5H_{11}$ | H | H | (Sm) 34 | 105 |
| n-$C_3H_7$ | n-$C_5H_{11}$ | H | $CH_3$ | 43 | 83 |
| n-$C_3H_7$ | n-$C_6H_{13}$ | H | H | 23 | 92 |
| n-$C_3H_7$ | n-$C_7H_{15}$ | H | H | 37 | 95 |
| n-$C_3H_7$ | n-$C_8H_{17}$ | H | H | (Sm) 28 | 89 |
| n-$C_3H_7$ | n-$C_9H_{19}$ | H | H | (Sm) 42 | 93 |
| n-$C_4H_9$ | n-$C_6H_{13}$ | H | H | (Sm) 38 | 86 |
| n-$C_4H_9$ | n-$C_7H_{15}$ | H | H | 34 | 91 |
| n-$C_4H_9$ | n-$C_8H_{17}$ | H | H | (Sm) 33 | 84 |
| n-$C_5H_{11}$ | n-$C_7H_{15}$ | H | H | 48 | 98 |
| n-$C_5H_{11}$ | n-$C_8H_{17}$ | H | H | 43 | 92 |
| $CH_2$-$CH_2$-CN | n-$C_4H_9$ | H | H | 71 | 105 |
| n-$C_5H_{11}$ | n-$C_9H_{19}$ | H | H | 54 | 94 |
| n-$C_6H_{13}$ | n-$C_7H_{15}$ | H | H | 47 | 86 |
| n-$C_6H_{13}$ | n-$C_8H_{17}$ | H | H | 37 | 84 |
| n-$C_6H_{13}$ | n-$C_9H_{19}$ | H | H | 59 | 87 |

It will be noted that all of the compounds in Table I have melting points (crystalline to smectic or to nematic transition point) below the desired temperature of 75° C.; and in fact, many of them are below 30° C. Moreover, the clearing points (nematic to isotropic liquid transition points) are in excess of 50° C. and, in many cases, above 80° C. By comparison, a symmetrical azine composition in which both $R_1$ and $R_2$ are alkyl radicals containing eight carbon atoms, the smectic to nematic transition temperature has been observed to be 68° C. with a nematic range of only 20° C.

The asymmetrical azine compounds of the present invention are also characterized by desirably low viscosity, expecially when formulated in mixtures for optical display purposes. Fast response or turn-off times result, as much as twice as fast as mixtures of ester liquid crystal compounds. For example, a display with an ester liquid crystal mixture showed a turn-off of about 140 microseconds, whereas a corresponding display employing a mixture of asymmetrical azine compounds according to the present invention exhibited a turn-off time of about 60 microseconds. Thus, the asymmetrical azine compounds of the present invention exhibit viscosities and turn-off times equivalent to commercial biphenyl liquid crystal compounds while, at the same time, possessing higher and more desirable isotropic transition temperatures. In addition, the asymmetrical azine compounds of the present invention exhibit improved chemical and photochemical stability over Schiff Base liquid crystal compounds, although not as great as biphenyl or ester liquid crystal compounds.

The asymmetrical azine compounds of the present invention can be combined in mixtures with other liquid crystal compounds as well as with other asymmetrical azine compounds using conventional methods such that the resulting composition exhibits a greater mesomorphic range than that of the individual compounds. In addition, asymmetrical azine compounds of the present invention, expecially those having melting points of 60° C. or higher, can be usefully combined with biphenyl liquid crystal compounds or with Schiff Base liquid crystal compounds or with ester liquid crystal compounds to elevate the transition temperature from the nematic phase to the isotropic liquid phase of the resultant mixture. The composition of one eminently useful mixture, according to the present invention is set forth in Table II below.

TABLE II

MIXTURE #1

| Compound | | | | |
|---|---|---|---|---|
| R | $R_1$ | X | Y | % by Weight |
| $C_3H_7$ | $C_6H_{13}$ | H | H | 14.3 |
| $C_3H_7$ | $C_5H_{11}$ | H | H | 19 |
| $C_4H_9$ | $C_6H_{13}$ | H | H | 14.3 |
| $C_1H_3$ | $C_4H_9$ | H | H | 9.5 |
| $C_1H_3$ | $C_8H_{17}$ | H | H | 9.5 |
| $C_3H_7$ | $C_8H_{17}$ | H | H | 14.3 |
| F | $C_3H_7$ | $CH_3$ | H | 14.3 |
| CN | $C_4H_9$ | $CH_3$ | H | 4.8 |

The nematic range of Mixture #1 is from −10° C. to 85° C.

A twisted nematic display requires the use of a liquid crystal mixture having a positive dielectric anisotropy; and for prior art liquid crystal compounds, this is ordinarily accomplished by utilizing a cyano (CN) group as one of the substituents, thus introducing a dipole along the long axis of the molecule. However, the asymmetrical azine compounds of the present invention inherently possess a mildly positive dielectric anistropy without need to resort to synthesis so as to incorporate a cyano group. However, when a display device with a low voltage threshold is to be fabricated, a cyano group is advantageously employed as one of the para-substituenst in the azine compounds of the present invention; and as will be noted, Mixture #1 contains such a compound. A twisted nematic display using Mixture #1 has displayed a threshold voltage of 2.8 volts. In addition to compositions employing two or more asymmetrical azine compounds, other compositions can be formulated using other types of liquid crystal material. For example, ten percent by weight of a cyano ester, specifically cyano-phenyl-pentyl benzoate, may be added to Mixture #1; and this latter composition has exhibited a nematic range of from −22° C. to 83° C. In a twisted nematic display, it exhibits a threshold voltage of 1.60.

The azine liquid crystal compounds of the present invention exhibit utility in a variety of mixtures with other types of liquid crystal materials. For instance, display devices behaving other than as a twisted nematic display and incorporating the instant azine compounds are described in Examples Nos. 1 and 7–9 below; and the instant azine compounds may be combined advantageously with a variety of liquid crystal materials of different classes as is set forth in all of Examples Nos. 1–9:

EXAMPLE NO. 1

A liquid crystal mixture having a negative dielectric anisotropy was made using 60% p-methoxybenzylidene-p-butylaniline (MBBA) and 40% p-ethoxybenzylidene-p'-butylaniline (EBBA). Both of these liquid crystal materials are available from a subsidiary of 3M Company, Vari-Light Corporation. This mixture had a nematic to isotropic transition temperature of 58.0° C. A cell was made using this mixture; and an electric field was applied across the electrodes. The cell exhibited properties of dynamic scattering.

Approximately 15% 4-n-propyl-4'-n-hexylbenzalazine was added to a portion of the foregoing MBBA-EBBA mixture. The new mixture exhibited a nematic to isotripic transition of temperature of 63.1° C. Again, a cell was fabricated using this latter mixture. An electric field was applied across the electrodes; and the mixture behaved as a negative liquid crystal, i.e. dynamic scattering was evident.

EXAMPLE NO. 2

A liquid crystal mixture was made using a material from BDH Chemical, Ltd. (Dorset, England) known as E-7 biphenyl. This material is a eutectic mixture of 51% 4-cyano-4'-n'pentylbiphenyl; 25% 4-cyano-4'-n-heptylbiphenyl; 16% 4-cyano-4'-n'octyloxybiphenyl; and 8% 4-cyano-4'pentyl-p-terphenyl. The E-7 biphenyl mixture is reported to have temperature range of −9° C. to +59° C. (G. W. Gray, Advances in Liquid Crystal Materials for Application, 1978 BDH publication).

A cell was made using a mixture of E-7 and 10% 4-n-propyl-4'-n-hexylbenzalazine; and its temperature range was found to be −10° C. to +66° C. In the twisted nematic cell, the electrooptic threshold was found to be 1.20 V rms as compared to E-7 alone which had a threshold of 1.15 V rms. The temperature range was thus significantly improved by the addition of the asymmetrical azine compound.

EXAMPLE NO. 3

A liquid crystal mixture was made using 28.2% trans-4-propyl-(4-cyanophenyl) cyclohexane; 42.4% trans-4- pentyl-(4-cyanophenyl)-cyclohexane; and 29.4% trans-4-heptyl-(4cyanophenyl)-cyclohexane. These phenylcyclohexane materials are available from E. Mark (Darmstadt, Germany). The above mixture showed a temperature range of −30° C. to +55° C. and an electrooptic threshold of 1.10 V rms.

To the above phenylcyclohexane mixture was added 40% 4-n-propyl-4'-hexylbenzalazine. In a twisted nematic cell, the mixture showed a temperature range of −50° C. to +73° C. and an electrooptic threshold of 1.30 V rms.

EXAMPLE NO. 4

A pyrimidine liquid crystal mixture was made using 40% 5-n-pentyl-2-(4-cyanophenyl)-pyrimidine and 60% 5-n-heptyl-2-(4-cyanophenyl)-pyrimidine. The above materials are available from Hoffmann-La Roche and Co., Ltd. (Basle, Switzerland). A twisted nematic cell was made using the above mixture with 10% 4-n-propyl-4'-n-hexylbenzalazine added. This latter mixture showed a temperature range of +30° C. to +51° C. and an electrooptic threshold of 0.85 V rms.

EXAMPLE NO. 5

A mixture containing asymmetrical alkyl benzalazines was prepared to measure the affect of cyanobiphenyl liquid crystals on the dielectric anisotrophy, i.e. the cyano and halide substituted benzalazines were not used. The mixture consisted of:

| | |
|---|---|
| 17.7% | 4-n-propyl-4'-n-hexylbenzalazine |
| 23.5% | 4-n-pentyl-4'-n-propylbenzalazine |
| 17.7% | 4-n-propyl-4'-n-octylbenzelazine |
| 17.7% | 4-n-butyl-4'-n-hexylbenzalazine |
| 11.7% | 4-n-hexyl-4'-n-methylbenzalazine |
| 11.7% | 4-n-methyl-4'-n-octylbenzalazine |

A sample cell of the twisted nematic type was made using the above mixture and it exhibited an electrooptical threshold of 6.2 V rms.

To a portion of the above azine liquid crystal mixture was added 5% of a material from BDH Chemical, Ltd., known as K-18 liquid crystal (4-cyano-4'-n-hexylbiphenyl). A sample cell, of the twisted nematic type, was made using this new mixture; and it exhibited an electrooptical threshold of 4.0 V rms. The combination of the K-18 material and the asymmetrical azine showed an improvement in the positive dielectric anisotropy.

EXAMPLE NO. 6

To the liquid crystal azine of Mixture #1 set forth hereinabove, there was added 0.5% each of Sudan Black, Sudan IV, and β-carotene and 2% cholesteryl nonanoate, as in U.S. Pat. No. 4,032,219 granted to J. Constant, I. Shanks and E. Raynes. A sample cell of the twisted nematic type was made using the resultant mixture; and 9 V rms voltage was applied across the electrodes. The display exhibited properties of similar displays as disclosed in U.S. Pat. No. 4,032,219.

EXAMPLE NO. 7

A sample cell was made using the same mixture as in Example #6, except that 5% cholesteryl nonanoate was added instead of 2%. This material, when activated by an appropriate electric field, behaved typically as would similar devices using the guest-host mechanism.

A sample cell using the mixture of this Example was made using parallel-parallel orientation; and the resultant device operated typically as would devices constructed in a similar manner.

A sample cell using the mixture of this Example was made using normal-normal orientation; and this device operated typically as would devices made in a similar manner.

EXAMPLE NO. 8

An asymmetrical azine liquid crystal mixture, Mixture #1 hereinabove, was made with the addition of 1% BDH D-77* [1,5-(4'-isopropyl)-anilino-anthraquinone], 1% BDH-D-5* [1-(4'-n-butyl) anilino-4-hydroxyanthraquinone] and 0.5% cholesteryl nonanoate. Sample cells were made up with twisted, parallel-parallel, and normal-normal orientation; and when an appropriate electric field was applied to the devices, they behaved in a manner typical of those described in the reference*.
*Photostable Anthroquinone Pleochroic Dyes, J. Constant, M. G. Pellath, and I. H. C. Roe; BDH Chemicals Ltd., Dorset, England, preprint of a paper presented at the Seventh International Liquid Crystal Conference (1978).

EXAMPLE NO. 9

An asymmetrical azine liquid crystal mixture, Mixture #1 hereinabove, was made with the addition of 5% cholesteryl nonanoate, 2.5% BHD D-37* [1,5-(4'-n-butyl) anilinoanthroquinone], and 0.5% BHD D-77* [1,5-(4'-isopropyl)-anilinoanthroquinone]. Sample cells were made in the twisted, parallel-parallel, and normal-normal orientation; and when an appropriate electric field was applied, the devices behaved typically as would similar devices of this general type.

The asymmetrical azine liquid crystal compounds of the present invention also show a very low order of birefringence; and thus, digital and other displays can be fabricated which are thin and possessed of fast response times without undesirable color variations such as mottling.

Although the classical preparation of a symmetrical azine compound typically involves reaction of a hydrazine with an excess of an aldehyde, the asymmetrical azines of the present invention are advantageously synthesized by first preparing the hydrazone of one of the components by use of the procedure of G. R. Newkome and D. L. Fishel (J. Org. Chem., 31, 677 [1966]). The reaction then proceeds as in the following typical equation:

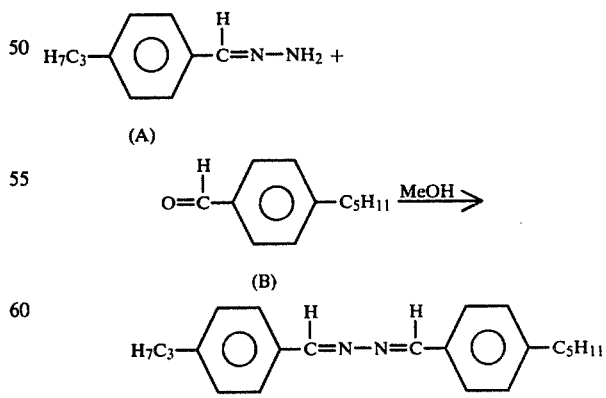

In the foregoing reaction, the hydrazone (A) which has been specifically prepared from n-propylbenzaldehyde, is mechanically mixed with the molecular equivalent weight of (B), n-pentylbenzaldehyde, in a suitable solvent such as methanol, for a period of about 15–30 minutes. The resulting azine product is then separated from the reaction mixture and purified by recrystallization.

In order that the principles of the present invention may be more readily understood, a physical embodiment thereof, applied to a light-control device or display, is shown in the accompanying drawing wherein FIG. 1 is a schematic, cross-sectional view showing an electrooptical display incorporating an asymmetrical azine liquid crystal composition according to the present invention.

Referring in detail to the drawing, a light-control device or shutter indicated generally by the reference numeral 10 is shown to comprise a first and a second planar light-transmitting member, 12 and 14. A thin film of liquid crystal material 16 is confined between the planar members 12 and 14; and in order to retain the liquid crystal material 16 in place, continuous liquid-stop ring 18 encompasses the liquid crystal material between the planar members 12 and 14. As will be appreciated, the ring 18 may be configured to define the perimeter of the numerical digit or other symbol which it is desired to illuminate selectively.

In order to provide external electrical connection to the liquid crystal material 16, the planar members 12 and 14, which are advantageously fabricated from a suitable glass, are coated on their confronting surfaces with thin conductive films 20 and 22 respectively. These films are advantageously fabricated of tin oxide and form respective electrodes for suitable attachment to an external electrical circuit 24. Circuit 24 comprises a direct current source 26, such as a battery, and a manual or other switching device 28. As will be appreciated, the planar members 12 and 14 are outwardly offset from the liquid stop ring 18 in order to facilitate connections with the circuit 24.

According to conventional practice, a polarizing filter 30 is applied to the outer plane surface of member 14. Similarly, a coating 32 is applied to the outer planar surface of member 12; and the coating 32 may be a cooperating polarizing filter with a reflective material such as metallic silver depending on whether it is desired that the device be transmissive or reflective. In addition, a light source 34 is focused on the polarizing filter 30; and in the case where the device 10 is reflective in nature, a viewing element 36, such as a photocell or the human eye, is disposed to observe the device 10 from the same aspect as light source 34.

In accordance with the present invention, the liquid crystal material 16 includes a compound which has a transition temperature of at least about 70° C., which has a melting point of no higher than about 60° C., and which comprises an asymmetrical azine liquid crystal compound as described hereinabove. Advantageously, the liquid crystal material 16 may take the form of Mixture #1 which has been described hereinabove.

In operation, when the switching device 28 is directed into a circuit-opening condition, the viewing element 36 will contemplate a bright background surrounding an opaque image of the indicia or other pattern created by the liquid crystal material 16. Contrariwise, when the switching device 28 is directed into a condition completing the circuit 24, the liquid crystal material 16 becomes light-transmissive, and the entire format of the device 10 appears reflective.

Various arrangements of light and dark areas may, of course, be created as circumstances make desirable. The term "light-control device" as used herein is intended to mean an optical gate for permitting or obstructing the passage of light.

The drawing and the foregoing disclosures are not intended to represent the only forms of our invention in regard to the details of fabrication and manner of application. Changes in the construction of display devices and in the formulation of liquid crystal compositions, as well as the substitution of equivalents, are contemplated as circumstances may suggest or render expedient; and although specific terms have been employed, they are intended in a generic and descriptive sense only and not for the purposes of limitation, the scope of the invention being delineated in the following claims.

The following is claimed as invention:

1. A light-control device comprising: first and second planar light-transmitting members; liquid crystal material confined between said members which comprises at least one nematic azine compound having a transition temperature from its nematic phase to its isotropic liquid phase of at least about 50° C. and a melting point from its crystalline phase to a liquid crystal phase of no higher than about 75° C., said nematic azine compound having the general formula:

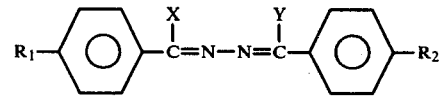

wherein $R_1$ and $R_2$ are different para-substituents whereby to produce an asymmetrical molecular structure, wherein $R_1$ and $R_2$ are selected from the group comprising cyano, halogen, alkyl, and substituted alkyl radicals in which the alkyl radical has from one to nine carbon atoms, and wherein X and Y are selected from the group comprising hydrogen and methyl radicals; and electrode means disposed in contact with said liquid crystal material.

2. A light-control device according to claim 1 wherein said liquid crystal material comprises two or more said azine compounds having asymmetrical molecular structure.

3. A light control device according to claim 1 wherein one of $R_1$ and $R_2$ is a cyano group.

4. A light-control device according to claim 1 wherein said liquid crystal material further includes a p'-cyanophenyl-p-alkylbenzoate.

5. A light-control device according to claim 4 wherein said p'-cyanophenyl-p-alkylbenzoate is p'-cyanophenyl-p-n-pentylbenzoate.

* * * * *